United States Patent [19]

Hutchinson, deceased et al.

[11] 4,025,567

[45] May 24, 1977

[54] PURIFICATION OF FLUORINATED ETHERS

[75] Inventors: William Milton Hutchinson, deceased, late of Bartlesville, Okla.; by Florence M. Hutchinson, executrix, Tahlequah, Okla.

[73] Assignee: Phillips Petroleum Company, Bartlesville, Okla.

[22] Filed: Nov. 20, 1974

[21] Appl. No.: 525,625

Related U.S. Application Data

[63] Continuation-in-part of Ser. No. 332,680, Feb. 15, 1973, abandoned.

[52] U.S. Cl. .................................. 260/616; 203/34; 203/42; 203/71
[51] Int. Cl.² ......................................... C07C 41/12
[58] Field of Search .......... 260/614 F, 616; 203/34, 203/42, 71

[56] References Cited

UNITED STATES PATENTS

| 2,500,388 | 3/1950 | Simons | 260/614 F |
| 2,519,983 | 8/1950 | Simons | 260/614 F |
| 3,650,917 | 3/1972 | Ruehlen | 204/59 F |
| 3,660,254 | 5/1972 | Dunn | 204/59 F |

*Primary Examiner*—Howard T. Mars

[57] ABSTRACT

A process for the purification of partially fluorinated dimethyl ethers to remove impurities from bis(difluoromethyl) ether and from difluoromethyl fluoromethyl ether by washing the ether-containing stream with sulfuric acid or hydrochloric acid. The acid extract is diluted with water to form two phases which can be separated.

19 Claims, 1 Drawing Figure

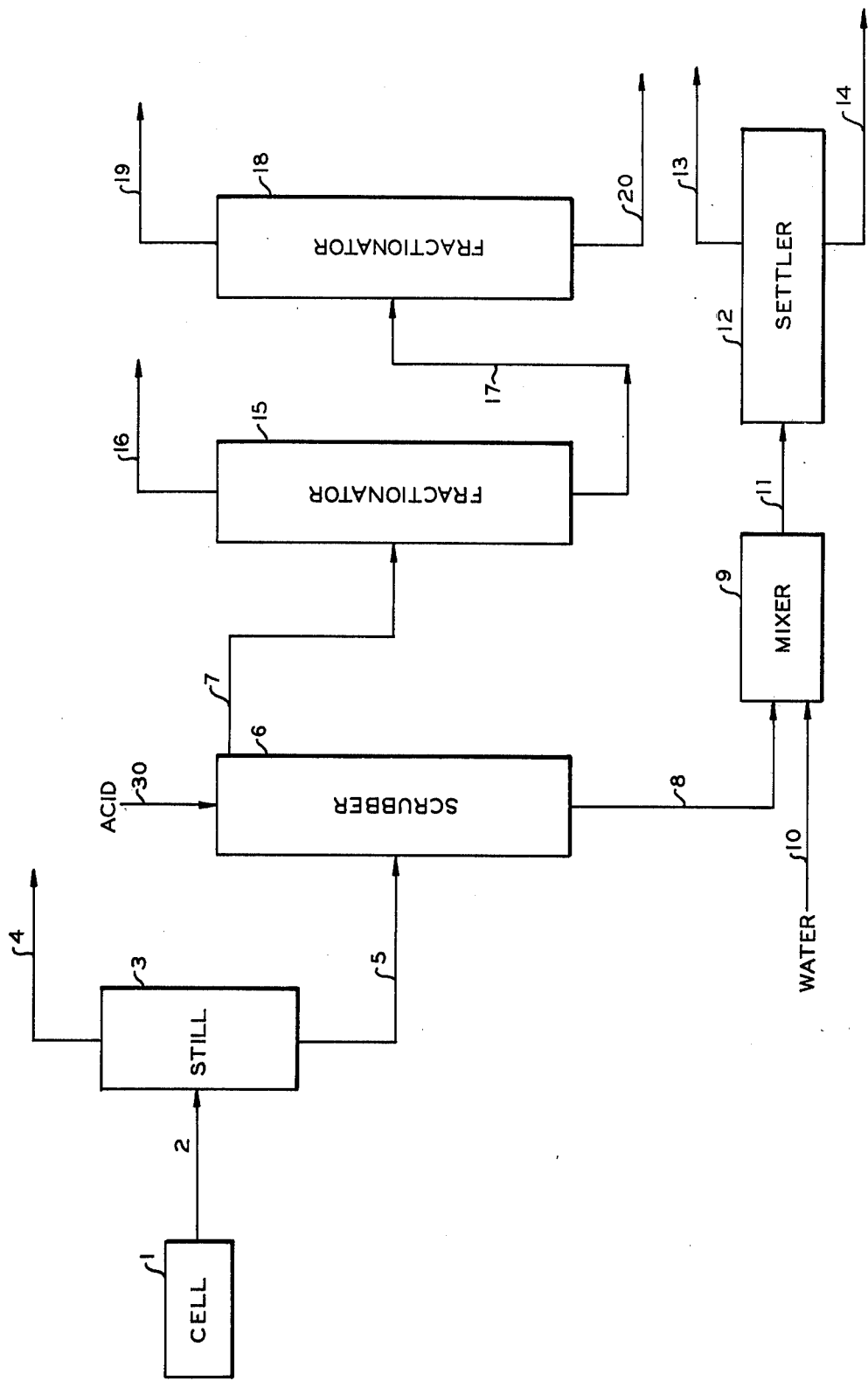

PURIFICATION OF FLUORINATED ETHERS

This application is a continuation-in-part application of my copending application for Ser. No. 332,680, filed Feb. 15, 1973, now abandoned.

This invention relates to the purification of fluorinated ethers.

In one of its more specific aspects, this invention relates to the separation and purification of those fluorinated ethers produced by electrochemical processes employing dimethyl ether as feed. In another aspect, this invention relates to the removal of impurities from partially fluorinated dimethyl ethers by washing with a mineral acid such as sulfuric acid or hydrochloric acid. In accordance with still another aspect, this invention relates to the water dilution of the mineral acid-containing phase obtained upon acid washing a partially fluorinated dimethyl ether-containing stream to effect further separation and recovery of a partially fluorinated dimethyl ether contained in the acid phase.

Electrochemical fluorination processes employing dimethyl ether as a feed are well known and disclosed in such patents as U.S. Pat. No. 2,500,388 to Simons, U.S. Pat. No. 3,660,254 to Dunn and U.S. Pat. No. 3,650,917 to Ruehlen, the disclosures of which patents are incorporated herein by reference. Such processes produce a product mixture comprising bis(trifluoromethyl) ether, difluoromethyl trifluoromethyl ether, bis(difluoromethyl) ether, difluoromethyl fluoromethyl ether, dimethyl ether and hydrofluoric acid.

Various factors complicate the separation of the product mixture, these factors including the presence of substantial amounts of hydrofluoric acid and dimethyl ether and the instability of the difluoromethyl fluoromethyl ether.

The method of the present invention solves this problem by contacting the cell product with a mineral acid such as sulfuric acid having a concentration of at least 65 weight percent or concentrated hydrochloric acid. This contact produces a raffinate or overhead that can be purified by distillation and an extract or bottoms which is then contacted with water to form two substantially immiscible liquid layers which are separable. In this way, hydrofluoric acid, dimethyl ether, difluoromethyl fluoromethyl ether and impurities are separated from the cell products in an extract from which difluoromethyl fluoromethyl ether is recovered by dilution with water.

The acid scrubbing procedure involved in the present invention is directed towards the removal of hydrofluoric acid and dimethyl ether from difluoromethyl trifluoromethyl ether and bis(difluoromethyl) ether and also to the removal of methylal and methyl formate from difluoromethyl fluoromethyl ether. Hydrofluoric acid, dimethyl ether, methylal, methyl formate and difluoromethyl fluoromethyl ether are soluble in sulfuric or hydrochloric acid but only the difluoromethyl fluoromethyl ether separates out in an appreciable amount on subsequent dilution of the acid extract with water.

It is understood that the acid absorption can be conducted at any reasonable temperature having an upper limit where decomposition of difluoromethyl fluoromethyl ether becomes excessive and a lower limit where viscosity of any stream involved hinders mixing or settling or where incomplete reaction of methylal or methyl formate causes its release on dilution of the extract. Temperatures of the extraction, holding, dilution or settling stages can be different. These operations can also be effected in a number of incremental stages. For example, a plurality of continuously-stirred contactors can be employed, interstage cooling being employed. Similarly, the extract can be further cooled either before or after water addition.

In general, the temperature for the sulfuric acid scrubbing will range from about −15° C to about 50 ° C with preferred temperature being in the range of about 0° C to about 20° C. The pressure in the scrubbing zone can vary appreciably but generally will be in the range of about 15 psia to about 100 psia. Similarly, the contact time can vary appreciably depending upon the concentration of impurities in the partially fluorinated dimethyl ether stream being treated, but generally will range from about 1 minute to about 1 hour. Also, the ratio of acid to ethers being treated can vary considerably but ordinarily will be from about 1:1 to about 10:1 lb. of acid per lb. of ethers.

The method of this invention will be more easily understood if explained in conjunction with the attached drawing which diagrammatically illustrates one embodiment of the invention.

Referring now to the attached drawing there is indicated electrochemical fluorination cell 1 employing a porous anode and from which there is produced a gaseous product of conventional analysis through conduit 2. The product is introduced into still 3 wherein suitable conditions of pressure and temperature are maintained at about 1 atmosphere pressure, about −58° C head temperature and about −20° C kettle temperature to separate an overhead product through conduit 4 and a bottoms product through conduit 5.

The conditions in still 3 will be such that light materials and bis(trifluoromethyl) ether is taken overhead and the remainder of the feed is removed as bottoms. The still conditions of temperature can vary somewhat, depending in part upon the still pressure, but generally the top temperature will be in the range of about −70° to about 0° C and the bottom temperature in the range of about −25° to about +25° C. The pressure can vary from 15 psia to 100 psia.

For convenience, the streams discussed herein will be designated by reference to that conduit through which they are conducted. Material balance around still 3 is then approximately as follows, based on 100 pounds of feed 2, as are all quantities specified herein.

| Component | Feed 2 | Over head 4 | Bottoms 5 |
|---|---|---|---|
| Lights | 1 | 1 | |
| $CF_3OCF_3$ [bis(trifluoromethyl) ether] | 8 | 8 | |
| $CHF_2OCF_3$ (difluoromethyl trifluoromethyl ether) | 10 | | 10 |
| $CHF_2OCHF_2$ [bis(difluoromethyl) ether] | 11 | | 11 |
| $CH_2FOCHF_2$ (difluoromethyl fluoromethyl ether) | 15 | | 15 |
| $CH_3OCH_3$ (dimethyl ether) | 40 | | 40 |
| HF (hydrofluoric acid) | 10 | | 10 |
| Others | 5 | | 5 |
| Total | 100 | 9 | 91 |

The term "Others" as employed herein will refer to those impurities sought to be removed from the fluorinated products, which impurities include compounds such as methyl formate and methylal, which distill with difluoromethyl fluoromethyl ether.

The overhead product comprising bis(trifluoromethyl) ether and lights is routed to disposal and bottoms product 5 comprising partially fluorinated dimethyl ethers and impurities is introduced into acid scrubber 6 into which about 120 pounds of commercial, concentrated sulfuric acid is introduced through conduit 30 countercurrently to the feedstream. The sulfuric acid will be employed in an amount at least equal to the total weight of the dimethyl ether and impurities designated "Others" introduced into scrubber 6. The sulfuric acid will have a concentration not less than about 65 and not more than about 105 weight percent $H_2SO_4$. In general, the acid will be introduced into contact with the bottoms product 5 in an amount within the range of from about 1 to 10 pounds per pound of bottoms product 5 although is no upper limit to the amount of acid which can be employed, other than practical considerations that the yield of desired products, particularly difluoromethyl fluoromethyl ether, is reduced with the employment of excess acid.

Extraction of the bottom product 5 with sulfuric acid can be made in any suitable manner which facilitates the production of the sulfuric acid-containing extract and a raffinate, such as batchwise or continuously in a plate-type scrubber, the contact time depending upon the ratio of acid to impurity content of the fluorocarbon containing stream to the scrubber. For example, at a ratio of 10 parts by weight of acid to 1 part by weight of impurities in the fluorocarbon stream, a temperature of about 5° C, a contact time of about 4 minutes is sufficient. By contact time is meant that period between the initial contact between the acid and the bottoms product and the initial contact between the bottoms extract stream and the water as hereinafter discussed.

The impurities are absorbed in the sulfuric acid in scrubber 6, which is maintained at about 1 atmosphere pressure and about 5° C, and there is separated overhead a gaseous phase through conduit 7 and an extract through conduit 8 which is routed to mixer 9. The streams leaving scrubber 6 are of the following approximate material balance in relation to stream 5 introduced thereinto.

| Component | Overhead 7 | Bottoms 8 |
|---|---|---|
| $CHF_2OCF_3$ | 10 | 0 |
| $CHF_2OCHF_2$ | 10 | 1 |
| $CH_2FOCHF_2$ | 5 | 10 |
| $CH_3OCH_3$ | — | 40 |
| HF | | 10 |
| Others | | 5 |
| $H_2SO_4$ | | 120 |
| Total | 25 | 186 |

Extract 8 is held in either the extractor or in a separate holding chamber (not shown) for a time sufficient to effect reaction of methylal and methyl formate with the sulfuric acid within the extract but insufficient to allow excessive decomposition of difluoromethyl fluoromethyl ether. The duration of the holding time is greater when more dilute sulfuric acid and lower holding temperatures are used, but may vary from 1 to 30 minutes at 5° C. The extract stream 8 is introduced into mixer 9 and water is introduced thereinto and thorough mixing of the two streams is effected. The temperature of mixing will generally be in the range of about 0° C to about 25° C. Preferably, this is done at a temperature of about 0° C.

Water can be introduced into contact with the sulfuric acid in any amount but will be introduced in at least an amount such that the concentration of $H_2SO_4$ in the resulting aqueous solution is not greater than 50 weight percent, that is, until dilution of the sulfuric acid extract causes the separation of that extract into two layers separable by gravity in settler 12. Generally, the sulfuric acid extract is diluted with from about 1 to about 5 volumes of water per volume of acid. However, the water is preferably employed in that amount which forms the maximum volume of the nonaqueous phase.

Water addition can be made at any point between the scrubber and the mixer with mixing being effected in any suitable manner. Water of commercial purity can be used.

Settling can be conducted in any suitable manner and for any suitable time in a quiescent zone to facilitate the formation of separable layers. For example, in the quantities employed in the exemplification used herein, a settling time of about 8 minutes at 0° C should suffice. Relatedly, a plurality of settling steps or accelerated settling such as centrifuging can be employed.

The mixture is transferred from mixer 9 through conduit 11 into settler 12 where two layers are allowed to separate, these layers being individually withdrawn to disposal through conduits 13 and 14 and having the following approximate material balance:

| Component | Product 13 | Product 14 |
|---|---|---|
| $CHF_2OCHF_2$ | 1 | 0 |
| $CH_2FOCHF_2$ | 6 | 4 |
| $CH_3OCH_3$ | 4 | 36 |
| HF | 0 | 10 |
| Others | | 5 |
| Water | 0 | 80 |
| $H_2SO_4$ | 0 | 120 |
| Total | 11 | 255 |

Product 13 can be separated into its components by distillation. $CH_3OCH_3$ and "Others" in Product 14 have reacted to form water-soluble products.

In this manner the impurities are removed from the fluorinated ethers.

The overhead product 7 comprising difluoromethyl trifluoromethyl ether, bis(difluoromethyl) ether and fluoromethyl difluoromethyl ether taken from scrubber 6 is routed into fractionator 15 which is operated at a pressure of about 1 atmosphere, a head temperature of about −34° C and a kettle temperature of about 10° C. The temperature in fractionator 15 can vary considerably, depending in part on the fractionator pressure, but generally will be within a range such that a substantial portion of the difluoromethyl trifluoromethyl ether is taken overhead and bis(difluoromethyl) ether and fluoromethyl difluoromethyl ether are removed as bottoms. Generally, a top temperature in the range of about −50° C to about 0° C and a bottom temperature in the range of about −10° C to about 25° C with a column pressure in the range of about 15 psia to about 100 psia will be satisfactory.

Two streams are separated, an overhead stream comprising difluoromethyl trifluoromethyl ether through conduit 16 and a bottoms stream comprising bis(difluoromethyl) ether and fluoromethyl difluoromethyl ether through conduit 17. The latter stream can be introduced into fractionator 18 which is operated at about 1 atmosphere pressure, a head temperature of about 7° C and a kettle temperature of about 35° C. The conditions in fractionator 18 can vary appreciably, but generally will be such that bis(difluoromethyl)

ether is taken overhead and fluoromethyl difluoromethyl ether is removed as bottoms. Generally, a top temperature of from about 0° to about 25° C and a bottom temperature of about 25° to about 50° C with a pressure of about 15 psia to 100 psia will be satisfactory. From fractionator 18 overhead stream 19 and bottoms stream 20 are separated.

Material balance analyses around fractionators 15 and 18 in relation to overhead stream 7 introduced into fractionator 15 are as follows:

| Component | Overhead 16 | Bottoms 17 | Overhead 19 | Bottoms 20 |
|---|---|---|---|---|
| $CHF_2OCF_3$ | 10 | | | |
| $CHF_2OCHF_2$ | | 10 | 10 | 0 |
| $CH_2FOCHF_2$ | | 5 | 0 | 5 |
| Total | 10 | 15 | 10 | 5 |

While the above description is of the preferred embodiment of the invention, it is to be understood that process steps other than those necessary, or ancillary, to the sulfuric acid contact step can be optionally carried out.

Additionally, other fractionation steps can be employed in addition to those previously described. Thus, stream 13 can be fractionally distilled to recover its components as individual streams.

It will be evident from the foregoing that various modifications can be made to the method of this invention. Such, however, are considered as being within the scope of the invention.

As disclosed hereinbefore difluoromethyl trifluoromethyl ether, bis(difluoromethyl) ether and dimethyl ether which cannot be separated by straight fractional distillation can be separated effectively by contacting the partially fluorinated ethers in vapor phase with concentrate hydrochloric acid at a reduced temperature and contacting conditions such that dimethyl ether is retained in the acid phase as the extract and difluoromethyl trifluoromethyl ether and bis(difluoromethyl) ether are recovered as raffinate substantially free of dimethyl ether. The dimethyl ether can be separated from the hydrochloric acid by heating the extract phase sufficiently to strip the dimethyl ether therefrom.

Although the contacting temperature can vary over a considerable range, it generally will be in the range of about −25° to about 50° C. In one embodiment, the mixture of ethers can be scrubbed vapor phase with concentrated hydrochloric acid at about 0° C. Recovery of dimethyl ether can be effected by adding water to the extract phase as with sulfuric acid or by heating the extract phase to a temperature in the range of about 50° to about 100° C. Although it is preferred to use concentrated hydrochloric acid, the concentration of the acid can vary from 20 to 45 weight percent. The raffinate phase comprising difluoromethyl trifluoromethyl ether and bis(difluoromethyl) ether can be separated by fractionation as described hereinbefore in connection with the sulfuric acid embodiment under conditions as set forth in the description of fractionation zones 15 and 18.

I claim:

1. A method for the purification and recovery of partially fluorinated dimethyl ethers from a mixture comprising difluoromethyl trifluoromethyl ether, bis(difluoromethyl) ether, difluoromethyl fluoromethyl ether, dimethyl ether, HF, and other impurities which comprises:

a. contacting said mixture with sulfuric acid having a concentration of at least 65 weight percent $H_2SO_4$ in an amount within the range of from about 1 to about 10 pounds of sulfuric acid per pound of said mixture at any reasonable temperature within an upper limit where decomposition of difluoromethyl fluoromethyl ether becomes excessive and a lower limit where viscosity of any stream involved hinders mixing or settling and at a pressure such that there is obtained a raffinate containing difluoromethyl trifluoromethyl ether, bis(difluoromethyl) ether, and fluoromethyl difluoromethyl ether, and an extract containing sulfuric acid, hydrofluoric acid, difluoromethyl fluoromethyl ether, dimethyl ether, and other impurities; and b. introducing water into said extract in an amount sufficient to form two substantially immiscible liquid layers which are separable by gravity and recovering as one layer sulfuric acid, hydrofluoric acid, dimethyl ether, and other impurities and as the second layer difluoromethyl fluoromethyl ether.

2. The method of claim 1 in which said mixture is contacted with a sulfuric acid stream containing an amount of sulfuric acid within the range of from about 65 to about 105 weight percent.

3. The method of claim 2 in which water is introduced into said bottoms product in an amount sufficient to form a sulfuric acid-containing solution in which the concentration of the sulfuric acid is not greater than 50 weight percent.

4. The method of claim 1 in which water is introduced into said bottoms product in an amount sufficient to form a sulfuric acid-containing solution in which the concentration of the sulfuric acid is not greater than 50 weight percent and the temperature of said contacting in (a) is in the range of from about 15° to about 50° C.

5. The method of claim 1 in which the raffinate obtained in step (a) is passed to a fractionation zone operated at about 15 psia to about 100 psia pressure and at a top temperature of about −50° to about 0° C and a bottom temperature of about −10° to about 25° C to obtain an overhead of purified difluoromethyl trifluoromethyl ether and a bottoms product containing bis(difluoromethyl) ether and difluoromethyl fluoromethyl ether.

6. The method of claim 5 in which said bottoms product is passed to a second fractionation zone operated at about 15 psia to about 100 psia pressure and a top temperature of about 0° to about 25° C and a bottom temperature of about 25° to about 50° C to obtain from said second fractionation as an overhead substantially pure bis(difluoromethyl) ether and as bottoms difluoromethyl fluoromethyl ether.

7. A method for separating difluoromethyl trifluoromethyl ether and bis(difluoromethyl) ether from a mixture also containing difluoromethyl fluoromethyl ether, dimethyl ether, hydrofluoric acid, and other impurities, which comprises contacting said mixture in an acid scrubber with sulfuric acid having a concentration of at least 65 weight percent $H_2SO_4$ in an amount within the range of from about 1 to about 10 pounds of sulfuric acid per pound of said mixture at any reasonable temperature within an upper limit where decomposition of difluoromethyl fluoromethyl ether becomes excessive and a lower limit where viscosity of any stream involved hinders mixing or settling and at a pressure such that there is obtained an extract containing sulfuric acid, hydrofluoric acid, difluoromethyl fluoromethyl ether, dimethyl ether, and other impurities and a raffinate containing difluoromethyl trifluoromethyl ether, bis(difluoromethyl) ether, and difluoromethyl fluoromethyl ether, and recovering said raffinate.

8. A method according to claim 7 wherein the sulfuric acid has a concentration of about 65 to about 105 weight percent $H_2SO_4$ and wherein the extraction is effected in said scrubber at a temperature of about −15° to about 50° C and at a pressure of about 15 psia to about 100 psia.

9. A method according to claim 7 wherein the difluoromethyl trifluoromethyl ether contained in said raffinate is separated by fractionation wherein the fractionating is conducted in a fractionator operated at a pressure of about 15 psia to about 100 psia, a top temperature in the range of about −50° to about 0° C, and a bottom temperature in the range of about −10° to about 25° C.

10. A method for separating difluoromethyl trifluoromethyl ether and bis(difluoromethyl) ether from a mixture also containing difluoromethyl fluoromethyl ether, dimethyl ether, hydrofluoric acid, and other impurities, which comprises contacting said mixture in an acid scrubber with sulfuric acid having a concentration of at least 65 weight percent $H_2SO_4$ in an amount within the range of from about 1 to about 10 pounds of sulfuric acid per pound of said mixture operated at a temperature in the range of about −15° to about 50° C and a pressure in the range of about 15 psia to about 100 psia such that there is obtained an extract containing sulfuric acid, hydrofluoric acid, difluoromethyl fluoromethyl ether, dimethyl ether, and other impurities and a raffinate containing difluoromethyl trifluoromethyl ether, bis(difluoromethyl) ether, and fluoromethyl difluoromethyl ether.

11. A method according to claim 10 wherein said raffinate is removed from said contacting and passed to a fractionation zone and therein subjected to fractionation conditions of a top temperature in the range of about −50° to about 0° C and a bottom temperature of about −10° to about 25° C and a pressure in the range of about 15 psia to about 100 psia sufficient to remove difluoromethyl trifluoromethyl ether overhead and bis(difluoromethyl) ether and fluoromethyl difluoromethyl ether as bottoms.

12. A method according to claim 10 wherein said extract is removed from said contacting and admixed with a sufficient amount of water to form a sulfuric acid-containing solution in which the concentration of sulfuric acid in the resulting aqueous solution is not greater than 50 weight percent, and said aqueous solution is allowed to separate into a fraction comprising fluoromethyl difluoromethyl ether and a fraction comprising water, sulfuric acid, HF, dimethyl ether, and other impurities.

13. A method according to claim 10 wherein said raffinate is removed from said contacting and passed to a fractionation zone and therein subjected to a top temperature in the range of about −50° to about 0° C and a bottom temperature of about −10° to about 25° C and pressure in the range of about 15 psia to about 100 psia sufficient to remove difluoromethyl trifluoromethyl ether overhead and bis(difluoromethyl) ether and fluoromethyl difluoromethyl ether as bottoms, and further wherein said extract is removed from said contacting and admixed with a sufficient amount of water to form a sulfuric acid-containing solution in which the concentration of sulfuric acid in the resulting aqueous solution is not greater than 50 weight percent, and said aqueous solution is allowed to separate into a fraction comprising fluoromethyl difluoromethyl ether and a fraction comprising water, sulfuric acid, HF, dimethyl ether, and other impurities.

14. A method for recovering by purification of partially fluorinated dimethyl ethers, difluoromethyl trifluoromethyl ether, and bis(difluoromethyl) ether which comprises passing said partially fluorinated dimethyl ethers to a still operated at about 15 psia to 100 psia, a top temperature of about −70° to about 0° C and a bottom temperature of about −25° to about 25° C, taking overhead lights, bis(trifluoromethyl) ether and as bottoms withdrawing difluoromethyl trifluoromethyl ether, bis(difluoromethyl) ether, difluoromethyl fluoromethyl ether, dimethyl ether, hydrofluoric acid, and other impurities, passing the bottoms to an acid scrubber operated at about −15° to about 50° C and about 15 psia to about 100 psia pressure and contacting said bottoms in said scrubber with sulfuric acid having a concentration of about 65 to about 105 weight percent $H_2SO_4$ in an amount within the range of from about 1 to about 10 pounds of sulfuric acid per pound of said bottoms passed to said scrubber such that there is obtained a raffinate containing difluoromethyl trifluoromethyl ether, bis(difluoromethyl) ether, and difluoromethyl fluoromethyl ether, passing said raffinate to a fractionator operated at about 15 psia to about 100 psia pressure and at a top temperature of about −50° to about 0° C and a bottom temperature of about −10° to about 25° C thus obtaining a first overhead of purified difluoromethyl trifluoromethyl ether and a second bottoms product containing bis(difluoromethyl) ether and difluoromethyl fluoromethyl ether, passing said second bottoms to a second fractionator operated at about 15 psia to about 100 psia pressure and a top temperature of about 0° to about 25° C and a bottom temperature of about 25° to about 50° C, and obtaining from said second fractionator as a second overhead substantially pure bis(difluoromethyl) ether.

15. A method for recovering by purification of partially fluorinated dimethyl ethers, difluoromethyl trifluoromethyl ether and bis(difluoromethyl) ether which comprises passing said partially fluorinated dimethyl ethers to a still operated at about 1 atmosphere pressure, an overhead temperature of −58° and a bottoms temperature of −20° C, taking overhead lights, bis(trifluoromethyl) ether and as bottoms withdrawing difluoromethyl trifluoromethyl ether, bis(difluoromethyl) ether, difluoromethyl fluoromethyl ether, dimethyl ether, hydrofluoric acid, and other impurities, passing the bottoms to an acid scrubber operated at about 5° C and 1 atmosphere pressure and contacting said bottoms in said scrubber with sulfuric acid having a concentration of about 65 to about 105 weight percent $H_2SO_4$ such that there is obtained an overhead raffinate containing difluoromethyl trifluoromethyl ether, bis(difluoromethyl) ether, difluoromethyl fluoromethyl ether, passing said raffinate to a fractionator operated at about 1 atmosphere pressure and at an overhead temperature of about −34 ° C and a bottoms temperature of about 10° C thus obtaining an overhead of purified difluoromethyl trifluoromethyl ether and a bottoms product containing bis(difluoromethyl) ether and difluoromethyl fluoromethyl ether, passing said bottoms to second fractionator operated at about 1 atmosphere pressure and overhead temperature of about 7° C and a bottoms temperature of about 35° C and obtaining from said second fractionator as an overhead substantially pure bis(difluoromethyl) ether.

16. A method for separating difluoromethyl trifluoromethyl ether and bis(difluoromethyl) ether from a mixture also containing difluoromethyl fluoromethyl ether, dimethyl ether, hydrofluoric acid, and other impurities, which comprises contacting said mixture in an acid scrubber in vapor phase with concentrated hydrochloric acid having a concentration of from 20 to 45 weight percent HCl operated at a temperature in the range of about −25° to about 50° C such that there is obtained a raffinate containing difluoromethyl trifluoromethyl ether and bis(difluoromethyl) ether and an extract containing dimethyl ether.

17. The method of claim 16 in which the raffinate obtained is passed to a fractionation zone operated at about 15 psia to about 100 psia pressure and a top temperature of about −50° to about 0° C and a bottom temperature of about −10° to about 25° C to obtain an overhead of purified difluoromethyl trifluoromethyl ether and a bottoms product containing bis(difluoromethyl) ether, passing said bottoms product to a second fractionation zone operated at about 15 psia to about 100 psia pressure and a top temperature of about 0° to about 25° C and a bottom temperature of about 25° to about 50° C and obtaining from said second fractionation zone as a second overhead substantially pure difluoromethyl ether.

18. A method according to claim 16 wherein said extract is heated to a temperature in the range of about 50° to about 100° C to strip dimethyl ether therefrom.

19. A method for recovering by purification of partially fluorinated dimethyl ethers, difluoromethyl trifluoromethyl ether and bis(difluoromethyl) ether which comprises passing said partially fluorinated dimethyl ethers to a still operated at about 15 psia to 100 psia, a top temperature of about −70° to about 0° C and a bottom temperature of about −25° to about 25° C, taking overhead lights, bis(trifluoromethyl) ether and as bottoms withdrawing difluoromethyl trifluoromethyl ether, bis(difluoromethyl) ether, difluoromethyl fluoromethyl ether, dimethyl ether, hydrofluoric acid, and other impurities, passing said bottoms to an acid scrubber operated at about −25° to about 50° C and contacting said bottoms in said scrubber in vapor phase with concentrated hydrochloric acid having a concentration of from 20 to 45 weight percent HCl such that there is obtained a raffinate containing difluoromethyl trifluoromethyl ether and bis(difluoromethyl) ether, and an extract containing dimethyl ether, passing said raffinate to a fractionation zone operated at about 15 psia to about 100 psia pressure and at a top temperature of about −50° to about 0° C and a bottom temperature of about −10° to about 25° C to obtain a first overhead of purified difluoromethyl trifluoromethyl ether and a second bottoms product containing bis(difluoromethyl) ether, passing said second bottoms product to a second fractionation zone operated at about 15 psia to about 100 psia pressure and a top temperature of about 0° to about 25° C and a bottom temperature of about 25° to about 50° C, and obtaining from said second fractionation as a second overhead substantially pure bis(difluoromethyl) ether, and heating said extract to a temperature in the range of about 50° to about 100° to strip dimethyl ether therefrom.

* * * * *